United States Patent [19]
Moore

[11] Patent Number: 5,935,526
[45] Date of Patent: Aug. 10, 1999

[54] CEILING FAN AIR FRESHENER

[76] Inventor: Joseph H. Moore, 6616 Brookfield Pl., Charlotte, N.C. 28270

[21] Appl. No.: 08/956,733

[22] Filed: Oct. 23, 1997

Related U.S. Application Data

[60] Provisional application No. 60/031,900, Nov. 25, 1996.

[51] Int. Cl.⁶ ..................................... A61L 9/12
[52] U.S. Cl. ............................ 422/124; 239/56; 239/57; 239/59; 416/5; 416/62; 416/146 R
[58] Field of Search .................. 422/123, 124; 239/56, 57, 59; 416/5, 62, 146 R

[56] References Cited

U.S. PATENT DOCUMENTS

| | | | |
|---|---|---|---|
| 3,214,065 | 10/1965 | Thornton | 239/59 |
| 4,145,001 | 3/1979 | Weyenberg et al. | |
| 4,666,670 | 5/1987 | Cox | 422/124 |
| 4,944,898 | 7/1990 | Glaser | 422/124 X |
| 5,022,819 | 6/1991 | Murcin et al | 416/62 |
| 5,141,707 | 8/1992 | Brite | 422/124 |
| 5,370,721 | 12/1994 | Carnahan | 422/124 X |
| 5,383,765 | 1/1995 | Baxter et al. | 422/124 X |
| 5,422,078 | 6/1995 | Colon | 422/124 X |
| 5,564,900 | 10/1996 | McAuley | 422/124 X |
| 5,624,230 | 4/1997 | Taylor et al. | 422/124 X |
| 5,775,876 | 7/1998 | Walker et al. | 416/62 |

*Primary Examiner*—E. Leigh McKane
*Attorney, Agent, or Firm*—Christopher C. Dremann

[57] ABSTRACT

An air freshener for attachment to a ceiling fan includes a storage container, a thick, porous fragrance cake impregnated with a fragrance secured inside the storage container, and "hook and loop" fasteners for attaching the storage container to the cover or a light fixture of the ceiling fan. The storage container preferably includes a bottom, a side wall and a lid. Together, the bottom and the side wall define a cavity in which the fragrance cake is secured. The lid is movable relative to the side wall so that the lid may be moved to expose the fragrance cake. The lid, the side wall or both have a plurality of apertures therethrough to permit ambient air to circulate around the fragrance cake to distribute the fragrance to the surrounding area as the air enters and exits the apertures and is further circulated by the ceiling fan. In an alternative embodiment, a thin, porous fragrance pad impregnated with a fragrance is attached to the underside of one or more of the blades of the ceiling fan near the root with "hook and loop" fasteners. In yet another embodiment, the lid of the storage container includes a grip for opening and closing the lid to selectively activate the air freshener to thereby extend the life of the fragrance cake.

5 Claims, 2 Drawing Sheets

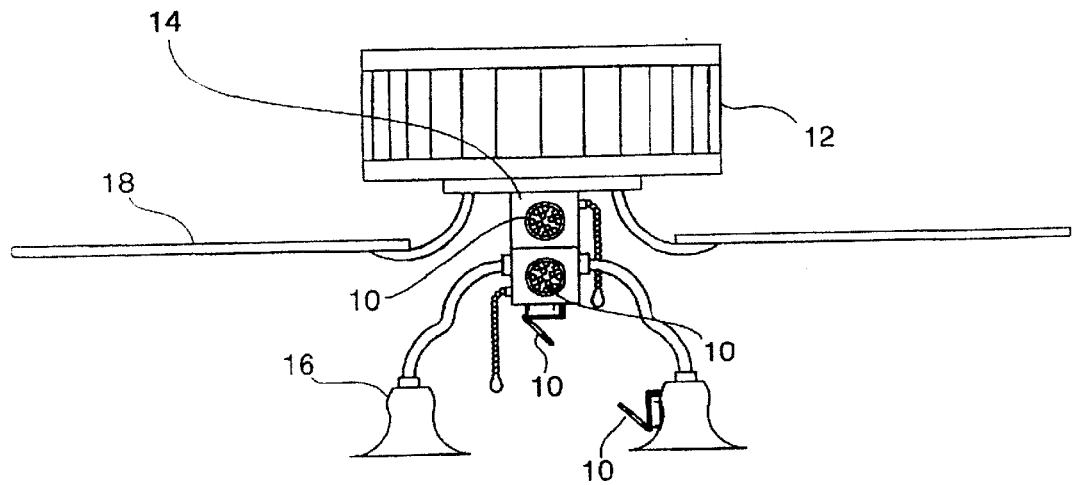
*Fig.1*
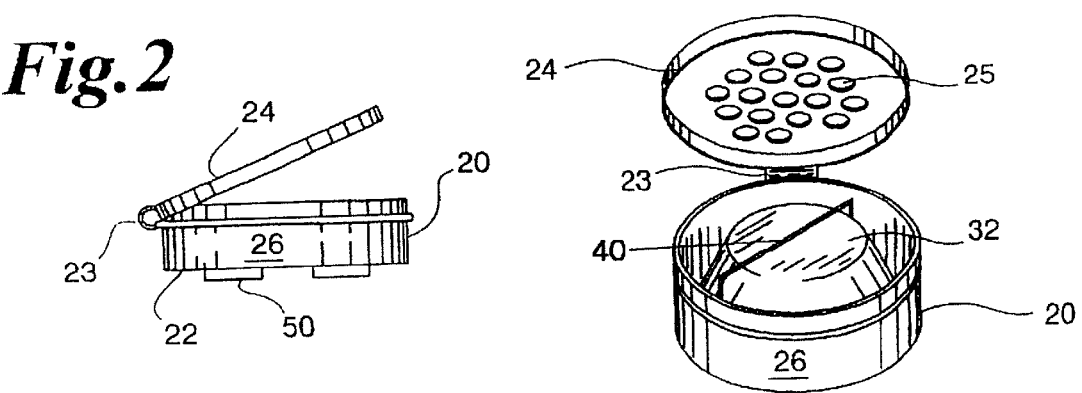
*Fig.2*  *Fig.2a*

CEILING FAN AIR FRESHENER

CROSS-REFERENCE TO RELATED APPLICATION

This application claims the benefit of U.S. Provisional Application No. 60/031,900 filed Nov. 25, 1996.

FIELD OF THE INVENTION

The present invention relates to air fresheners, and more particularly, to an air freshener attachable to a ceiling fan.

BACKGROUND OF THE INVENTION

Air fresheners for eliminating odors and dispensing a pleasant fragrance are well known. Two common types of air fresheners are a thin, paper disc which is impregnated with a fragrance, and a thick, porous cake which is impregnated with a fragrance. The disc or cake is placed in a decorative storage container and attached to a stationary surface, for example in a room or inside a vehicle. The storage container is open to the surrounding atmosphere, or is furnished with one or more vents that may be opened so that the fragrance is dispensed into the room or vehicle. Typically, the storage container is reusable and the disc or cake is replaced periodically when the fragrance is completely dispensed.

U.S. Pat. No. 5,269,723 issued Dec. 14, 1993, to Bender discloses a vehicle air freshener for dispensing a pleasant fragrance to the passenger compartment of a vehicle. The air freshener is installed into the ventilation system of the vehicle behind an air vent in the passenger compartment. The air freshener includes an elongate, cylindrical tube which is sized to fit through one of the openings in the grill of the air vent. The air freshener includes a handle which is wider than the openings in the grill to prevent the air freshener from falling into the air duct. Because the fragrance is contained inside the elongate tube, only a small portion of the air flow through the ventilation system absorbs and distributes the fragrance. Accordingly, a separate air freshener must be placed behind each air vent of the ventilation system to obtain a uniform distribution of the fragrance throughout the entire passenger compartment of the vehicle.

U.S. Pat. No. 4,808,347 issued Feb. 28, 1989, to Dawn and U.S. Pat. No. 5,373,581 issued Dec. 13, 1994, to Smith each disclose an air freshener which is plugged into the cigarette lighter of the vehicle. The air freshener disclosed in the patent to Smith includes an electric heating element powered by the cigarette lighter of the vehicle for vaporizing a porous fragrance cake. The fragrance is distributed to the passenger compartment of the vehicle by circulation of the ambient air. The patent to Dawn discloses a fan positioned behind a porous fragrance cake which is driven by an electric motor powered by the cigarette lighter of the vehicle. Operation of the fan distributes the fragrance to the passenger compartment of the vehicle.

U.S. Pat. No. 4,258,004 issued Mar. 24, 1981, to Valenzona et al. discloses a hollow, disc-shaped storage container. The container is attached to a flat surface at a suitable location in a room or inside the passenger compartment of the vehicle. One or more fragrance discs are placed inside the container, and the top of the container is rotated relative to the bottom to create openings in the side wall of the container. The openings permit the fragrance to be distributed to the room or to the passenger compartment of the vehicle by circulation of the ambient air.

The Bender air freshener relies on the ventilation system of the vehicle to distribute the fragrance throughout the passenger compartment. The Dawn air freshener utilizes an electric fan to distribute the fragrance to the passenger compartment. The Smith and Valenzona air fresheners rely on the circulation of the ambient air in the room or inside the passenger compartment of the vehicle to distribute the fragrance. Thus, in a large room or vehicle, these known air fresheners are not efficient in distributing the fragrance throughout the entire room or passenger compartment.

Although these, and other, air fresheners are known, the prior art air fresheners do not evenly distribute a fragrance throughout an open area, such as a large room. Accordingly, it is apparent that an air freshener is needed which uniformly distributes a fragrance throughout an entire room. Further, none of the prior art air fresheners provides a convenient, disposable means for attaching an air freshener to a ceiling fan. Accordingly, it is apparent that a storage container for an air freshener is needed which can be attached to a ceiling fan.

Accordingly, one of the objects of the present invention is to provide an air freshener for distributing a fragrance evenly throughout an open area, such as a large room.

It is a more particular object of the invention to provide an air freshener which can be attached to a ceiling fan, so that the operation of the ceiling fan will distribute the fragrance of the air freshener throughout the entire room.

It is a further object of the invention to provide a storage container for conveniently attaching a fragrance disc or cake to a ceiling fan.

It is another object of the invention to provide a storage container which is reusable so as to permit a fresh fragrance disc or cake to be attached to the ceiling fan so as to continuously distribute a fragrance to an entire room at minimal cost.

SUMMARY OF THE INVENTION

The present invention is an air freshener for attachment to a ceiling fan. The invented air freshener includes a storage container having at least one fragrance means, impregnated with a fragrance, positioned therein. The fragrance means is preferably either a fragrance cake or a fragrance disc.

The invented air freshener also includes an attachment means for attaching the storage container to the ceiling fan so that the ceiling fan rapidly and uniformly distributes the fragrance throughout a surrounding open area. An exemplary attachment means is a "hook and loop" type fastener having a first piece attached to the storage container and a second piece attached to the ceiling fan for removably securing the storage container to the ceiling fan. In a preferred embodiment, the attachment means attaches the storage container to a stationary portion of the ceiling fan, such as the ceiling fan cover or the light fixture of the ceiling fan.

The storage container has a cavity defined by a bottom and a continuous side wall integrally formed with the bottom. The cavity is enclosable with a removable lid that provides access to the cavity to replace the fragrance means. In one embodiment, the storage container lid is hinged to the side wall. Preferably, apertures in provided the side wall and/or lid permit dissipation of the fragrance from the storage container.

The fragrance means can be secured within the storage container cavity if necessary to prevent the fragrance means from falling out. This is especially necessary when the storage container is positioned in an inverted manner. Preferably, the fragrance means and the side wall form an interference fit which secures the fragrance means in the cavity. Alternatively, a pair of elastic retaining springs having opposed ends diametrically fixed to the side wall which secure the fragrance means in the cavity.

Activation means are also included to regulate the dissipation of fragrance through the apertures. In a preferred embodiment, the activation means is a removable cover positionable over some or all of the apertures. An adhesive backing on the removable cover enables the cover to be moved from a first position covering the apertures to a second position exposing some or all of the apertures.

In an alternate embodiment, thin porous felt pads are impregnated with a liquid fragrance. The pads are then attached to the underside of one or more of the ceiling fan blades using for example, the "hook and loop" fastener previously described.

In another embodiment, the storage container has an inner side wall and an outer side wall adjacent the inner side wall. The activation means includes a first lip extending radially outwardly from a lower edge of the inner side wall and a second lip extending radially inwardly from an upper edge of the outer side wall. The outer side wall is movable relative to the inner side wall between a fully closed position and a fully open position wherein the second lip overlaps the first lip. Thus, the apertures in the side wall are covered when the side wall is in the closed position and are exposed when the side wall is in the open position. A grip, extending generally perpendicular from the storage container, can be included to move the outer side wall between the fully closed position and the fully open position.

Additional air tight storage containers can be included for storing one or more replacement fragrance means therein. As a result, once a fragrance means has been fully dissipated, it can be discarded and then replaced with a fresh fragrance means.

BRIEF DESCRIPTION OF THE DRAWINGS

In view of the above mentioned objects and others which will more readily appear as the nature of the invention is better understood, the invention is embodied in the novel combination and arrangement of parts hereinafter more fully described, illustrated and claimed with reference being made to the attached drawings, in which:

FIG. 1 is an elevation view of a conventional ceiling fan having several air fresheners according to the invention attached thereto;

FIG. 2 is an elevation view of a preferred embodiment of one of the air fresheners of FIG. 1;

FIG. 2a is a perspective view of the air freshener of FIG. 2 showing the fragrance cake inside the storage container;

DETAILED DESCRIPTION OF THE PREFERRED EMBODIMENTS

Figure 3:
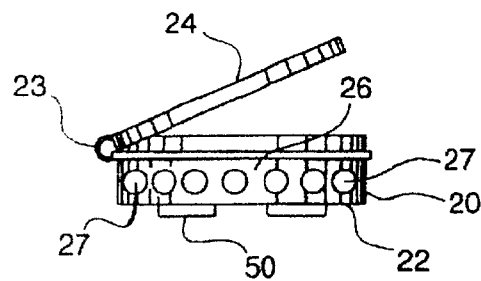
FIG. 3 is an elevation view of an alternative embodiment of an air freshener according to the invention.

The invention is an air freshener, indicated generally at 10, which is attached to a conventional ceiling fan 12 to evenly distribute a fragrance throughout an open area, such as a large room. In the preferred embodiment illustrated in FIGS. 1, 2 and 2a, the air freshener 10 comprises a storage container 20, a fragrance means 30, a means 40 for securing the fragrance means inside the storage container and a means 50 for attaching the air freshener to the ceiling fan.

Fragrance means 30 may be any means for dissipating a fragrance, but preferably, is a fragrance disc or fragrance cake. By fragrance disc what is meant is a thin, porous disc made of paper or cloth which is impregnated with a fragrance. By fragrance cake what is meant is a thick, porous cake made of a poly cone or crystal-like substance which is pressed into a tablet and impregnated with a fragrance. As air passes through the pores in the disc or cake, the fragrance is dissipated into the surrounding area by circulation of the ambient air. As illustrated in FIG. 2a, the fragrance means 30 is preferably a fragrance cake 32. A suitable fragrance cake 32 is available from Flavors & Fragrances Specialty Company, Franklin Lake, N.J.

The storage container 20 is sized appropriately to secure at least one fragrance means 30 therein. A similar air-tight storage container (not shown) may be provided for storing one or more replacement fragrance means 30 therein when not in use. A preferred embodiment of a storage container 20 according to the invention is shown in FIG. 2 and FIG. 2a. A suitable storage container is the Scents-It™ air freshener unit available from Airkem Professional Products, St. Paul, Minn. As best shown in FIG. 2a, the storage container 20 is sized and shaped to accept a fragrance cake 32 therein. Thus, the storage container 20 is generally circular. However, storage container 20 may be any shape, such as rectangular or square, which is suitable for securing the pre-selected fragrance means 30 therein.

Preferably, the storage container 20 is constructed in the form of a box. Accordingly, the storage container 20 includes a bottom, a top or lid, and at least one continuous side wall. The bottom is integral with the side wall so as to define a cavity in the storage container 20 for receiving the fragrance means 30 therein. In the preferred embodiments shown in FIGS. 2, 2a and 3, the storage container 20 includes bottom 22, lid 24 and continuous side wall 26. The bottom 22 and the side wall 26 together define a cavity 28 in storage container 20 for receiving the fragrance cake 32 therein.

Preferably, the storage container 20 further comprises at least one hinge 23 for hinging the lid 24 to the side wall 26. Thus, the lid 24 may be lifted to provide access to the cavity 28 to replace the fragrance cake 32. The hinged lid 24 may be left open to permit a greater amount of ambient air to circulate through and around the porous cake, thus increasing the rate of dissipation of the fragrance. The lid 24 may also be removably fixed to the side wall 26 by any means to close the cavity 28 of the storage container 20. Preferably, however, the lid 24 comprises a lip which cooperates with a groove provided on the side wall 26 in a conventional manner to removably secure the lid to the side wall.

As best shown in FIG. 2a, the fragrance cake 32 is positioned in the cavity 28 defined by the bottom 22 and the side wall 26 of the storage container 20. The fragrance cake 32 is secured within the storage container 20 by securing means 40. Securing means 40 may be any means for securing the fragrance cake 32 inside the storage container 20. Preferably, the fragrance cake 32 is suitably shaped and sized so that the fragrance cake and the inner surface of side wall 26 have a slight interference fit. Thus, the fragrance cake 32 is retained in cavity 28 even when the storage container 20 is inverted for attachment to the underside of the ceiling fan 12 (FIG. 1). Alternatively, for example, securing means 40 may comprise a metallic, elastic retaining spring having opposed ends which are fixed to opposite sides of the side wall 26. Thus, the fragrance cake 32 is removably retained within the cavity 28 of the storage container 20 when in use.

The storage container 20 further comprises a plurality of apertures 25 formed in the lid 24. As illustrated in FIG. 3, the storage container 20 may further comprise a plurality of apertures 27 formed in the side wall 26. The size and number of apertures 25 and 27 may be selected to increase or decrease the amount of ambient air which circulates through and around the porous fragrance cake 32, and to thereby vary the rate of dissipation of the fragrance from the cake. A thin, removable cover (not shown) having an adhesive backing thereon is preferably positioned over the lid 24 to cover apertures 25 when the air freshener 10 is not in use. The adhesive backing permits the cover to be repositioned to cover one or more holes during use to thereby further vary the rate of dissipation of the fragrance. A similar elongate, thin, removable cover (not shown) is preferably positioned over the side wall 26 to cover apertures 27 in a like manner for the same purpose.

The fragrance impregnated in the cake 32 dissipates into the ambient air and is distributed to the surrounding area as the ambient air entering and exiting apertures 25 and 27 of storage container 20 circulates through and around the porous fragrance cake 32. Naturally, the rate of dissipation depends on the rate of circulation of the ambient air, which may be varied as previously described. Increasing the rate of circulation of the ambient air in the immediate vicinity of the fragrance cake 32 results in the fragrance dissipating from the cake at an increased rate. Thus, increasing the rate of circulation of the ambient air requires the fragrance cake 32 to be replaced more frequently.

An important advantage of the invention over known air fresheners is that the air freshener 10 is attached to the stationary cover 14 or a light fixture 16 of the ceiling fan 12. Thus, the rate of circulation of the ambient air in the immediate vicinity of the air freshener 10 is not significantly increased when the ceiling fan is in operation. In contrast, the rate of circulation of the ambient air remote from the air freshener 10 is substantially greater. The fragrance dissipated by the air freshener 10 is therefore distributed rapidly and evenly to the surrounding area. Accordingly, the air freshener 10 uniformly distributes a pleasant fragrance to an open area, such as a large room, without the need to replenish the fragrance cake 32 at frequent intervals, and without producing a heavy concentration of the fragrance in the immediate vicinity of the air freshener.

The air freshener 10 further comprises attachment means 50 for attaching the storage container 20 to the conventional ceiling fan 12. With respect to the preferred embodiments illustrated in FIGS. 1–3, it is important to note that the storage container 20 is attached to a stationary portion of the ceiling fan 12, such as the cover 14 or a light fixture 16 (FIG. 1) for the reason previously discussed. Attachment means 50 may be any means for securely attaching the storage container 20 to the ceiling fan 12, such as double-sided tape or a "hook and loop" type fastener commonly referred to by the brand name VELCRO®.

It has been determined, however, that the best results are obtained when attachment means 50 comprises one or more strips of an adhesive-baked, heavy duty VELCRO®. One half of the VELCRO® strip is adhered to a substantially flat surface on a stationary portion of the ceiling fan. The other half of the VELCRO® strip is adhered to the underside of the bottom 22 of the storage container 20. The air freshener 10 is then secured to the ceiling fan 12 by engaging the opposing "hook and loop" strips of VELCRO®. In this manner, the storage container 20 is easily removed for replacement or to replenish the fragrance cake 32, and the external surface of the ceiling fan 12 is not damaged from repeated applications of double-sided tape.

As previously discussed, the storage container 20 is preferably attached to a substantially flat, exterior surface on a stationary portion of the ceiling fan 12. It has been determined that attaching the storage container 20 to a blade 18 of the ceiling fan 12 is undesirable. In addition to the advantages of stationary mounting previously discussed, the centrifugal force developed by rotation of the blade 18 of the ceiling fan 12 can overcome attachment means 50 and cause the storage container 20 to become detached and unexpectedly fly into the surrounding area away from the fan. Further, the extra weight of the storage container 20 and fragrance means 30 on the blade 18 can unbalance the blade set and cause serious damage to the motor of the ceiling fan. Accordingly, as shown in FIG. 1, it is preferred that one or more of the preferred embodiments of the air freshener 10 illustrated in FIGS. 1–3 be attached to the stationary cover 14 or light fixture 16 of the ceiling fan 12.

Figure 4:
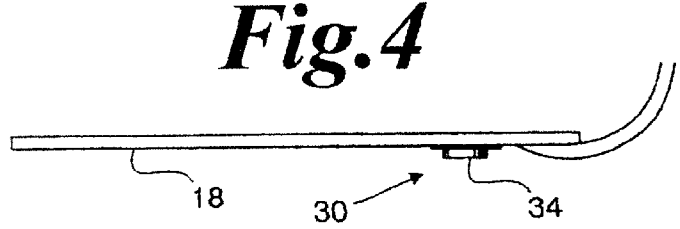
FIG. 4 is an elevation view of a typical blade of a conventional ceiling fan having another alternative embodiment of an air freshener according to the invention attached thereto.
Figure 5:
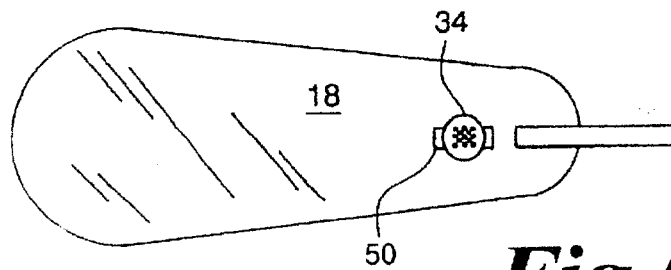
FIG. 5 is a plan view of the typical blade and alternative embodiment of the air freshener of FIG. 4.

FIG. 4 and FIG. 5 illustrate an alternative embodiment of an air freshener according to the invention which overcomes the aforementioned difficulties. The air freshener 10 illustrated in FIG. 4 and FIG. 5 comprises fragrance means 30 and attachment means 50. In this alternative embodiment, however, fragrance means 30 comprises a thin, porous pad 34 made of felt which is impregnated, for example by soaking the pad with a liquid fragrance, such as pine or lemon oil. The pad 34 is preferably attached to at least one fan blade 18 of the ceiling fan 12 near the root of the blade. Although the pad 34 does not weigh enough to significantly alter the balance of the blade set, it is desirable to attach a pad 34 to each of the fan blades 18 so that the balance of the blade set is maintained.

In this alternative embodiment, attachment means 50 comprises double-sided tape or opposed strips of VELCRO®. However, as previously discussed, at least one strip of VELCRO® is preferred so that the pad 34 may be easily removed and replaced, or removed to replenish the liquid fragrance. The liquid fragrance may be replenished on the fragrance pad 34 by simply wiping, dripping or spraying a sufficient amount of the fragrance onto the pad. As shown, attachment means 50 is adhered to the underside of the blade 18. Thus, the fragrance pad 34 is inverted. In the event that an excess amount of liquid fragrance is applied to the pad 34 such that the liquid fragrance drips from the pad, the air freshener 10 may be attached to the upper side of the blade 18. The location of the air freshener 10 depicted in FIG. 4 and FIG. 5 is shown as the preferred location for convenience of installation only. The size, number and location of the pad or pads 34 is not limited in any manner.

Figure 6:
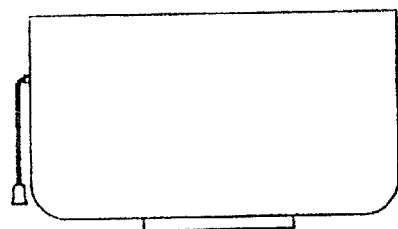
FIG. 6 is an elevation view of the cover of a conventional ceiling fan having yet another alternative embodiment of an air freshener according to the invention attached thereto.
Figure 7:
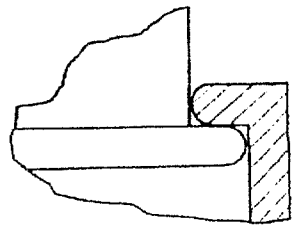
FIG. 7 is a detail view of a portion of the alternative embodiment of the air freshener of FIG. 6.

FIGS. 6 and 7 illustrate yet another alternative embodiment of an air freshener 10 according to the invention. As shown, the air freshener 10 is inverted and attached to the underside of the cover 14 of a conventional ceiling fan 12. As previously discussed, the air freshener 10 comprises attachment means 50, preferably heavy duty VELCRO®, for securing the air freshener to the exterior surface of the cover 14 of the ceiling fan 12.

In this alternative embodiment, the air freshener 10 further comprises activating means 60 for exposing the apertures 27 formed in the sidewall 26 of the container 20. Preferably, activating mean 60 comprises a grip 62 extending generally perpendicular to lid 24 of container 20. Grip 62 may be secured to lid 24 in any convenient manner, but is preferably integrally molded with the lid or is secured by a screw from the underside of the lid. Grip 62 is provided so that apertures 27 may be selectively exposed or covered as desired, thus extending the service life of the fragrance means 30 (not shown) secured therein.

As best shown in FIG. 7, activating means 60 comprises a lip 64 that extends radially outwardly from the lower edge of the side wall 26 of the container 20. Activating means 60 further comprises a corresponding lip 66 that extends radially inwardly from the upper edge of the lid 24. Thus, when lid 24 is lowered from its fully closed position over lip 68, which like lip 64 extends radially outwardly from the upper edge of the side wall 26 of the container 20, lip 66 catches and rests against lip 64. In this configuration (as shown), lid 24 is in the fully open position and the fragrance mean 30 dissipates into the surrounding area as previously described. Preferably, lid 24 and container 20 are made of a soft, resistent plastic so that the lid may be repeatedly opened and closed to activate the air freshener 10.

As is now apparent from the preceding description and the accompanying drawings, the invention provides an air freshener for attachment to a stationary portion of a conventional ceiling fan which evenly distributes a pleasant fragrance to the surrounding area, such as a large room. The invention further provides a storage container for a fragrance disc or cake which is removably attached to the ceiling fan so that the entire storage container may be replaced, or only the fragrance disc or cake may be replenished. In an alternative embodiment, the invention provides a fragrance pad having a dispensable liquid fragrance and which is removably attached to a blade of the ceiling fan so that the pad may be removed and replaced, or the liquid fragrance replenished.

Obviously, many alternative configurations and modifications of the invention are within the level of ordinary skill of those accomplished in the art of air freshener design. Thus, it is to be understood that the invention is not intended to be limited to the preceding description of the preferred embodiments, or by the preferred embodiments illustrated in the accompanying drawings, but rather is intended to encompass all embodiments within the spirit and scope of the invention disclosed herein.

That which is claimed is:

1. An air freshener for attachment to a ceiling fan, said air freshener comprising a storage container defining a hollow cavity and comprising a base having a first continuous side wall integrally formed therewith and depending therefrom, said first side wall having a first lip extending outwardly therefrom and having at least one aperture therethrough, a lid opposite said base, said lid having a second continuous side wall integrally formed therewith and depending therefrom, said second side wall having a second lip extending inwardly therefrom, wherein said lid is movable relative to said base between a fully closed position wherein said second side wall covers said at least one aperture, and a fully open position wherein said second lip is in contact with said first lip and said at least one aperture is exposed;

a fragrance means impregnated with a fragrance and positioned within the cavity defined by said storage container; and attachment means for attaching the base of said storage container to a stationary portion of a ceiling fan so that the ceiling fan uniformly distributes the fragrance of said fragrance means throughout a surrounding open area.

2. The air freshener of claim 1 wherein said stationary portion of the ceiling fan is selected from the group consisting of a ceiling fan light fixture, a ceiling fan cover and an exterior surface on the underside of the ceiling fan cover.

3. The air freshener of claim 1 wherein said fragrance means is selected from the group consisting of a fragrance disc and a fragrance cake.

4. The air freshener of claim 1 wherein said storage container further comprises a grip extending generally perpendicular from said lid for moving said second side wall between said fully closed position and said fully open position.

5. The air freshener of claim 1 wherein said attachment means comprises a hook and loop fastener having a first piece attached to said storage container and a second piece attached to the ceiling fan for removably securing said storage container to the ceiling fan.

\* \* \* \* \*